United States Patent [19]
Reimels et al.

[11] Patent Number: 5,925,045
[45] Date of Patent: Jul. 20, 1999

[54] BIPOLAR ELECTROSURGICAL INSTRUMENT

[75] Inventors: Harry G. Reimels, Braintree; Raymond Morrison, Scituate, both of Mass.

[73] Assignee: Mentor Corporation, Santa Barbara, Calif.

[21] Appl. No.: 08/831,924

[22] Filed: Apr. 2, 1997

Related U.S. Application Data

[62] Division of application No. 08/591,953, Jan. 23, 1996., which is a continuation of application No. 08/150,925, Nov. 10, 1993., abandoned.

[51] Int. Cl.$^6$ ............................. A61B 17/38; A61B 17/36
[52] U.S. Cl. .................... 606/48; 606/49; 606/50; 427/2.12; 427/2.28; 604/20
[58] Field of Search ...................... 427/2.1, 2.12, 427/2.28, 77, 78, 80, 81, 124, 125, 250, 105; 606/29, 48, 50, 49; 604/20

[56] References Cited

U.S. PATENT DOCUMENTS

| | | |
|---|---|---|
| 1,814,791 | 7/1931 | Ende . |
| 1,916,722 | 7/1933 | Ende . |
| 2,249,894 | 7/1941 | Goldenstein . |
| 3,357,858 | 12/1967 | Gravey . |
| 3,397,085 | 8/1968 | Cariou et al. . |
| 3,461,058 | 8/1969 | Haley, Jr. et al. . |
| 3,503,799 | 3/1970 | Aoki et al. . |
| 3,808,049 | 4/1974 | Caley et al. . |
| 3,858,586 | 1/1975 | Lessen . |
| 3,900,600 | 8/1975 | Spaulding . |
| 4,043,342 | 8/1977 | Morrison, Jr. . |
| 4,476,862 | 10/1984 | Pao . |

(List continued on next page.)

FOREIGN PATENT DOCUMENTS

| | | |
|---|---|---|
| 0067680 | 12/1982 | European Pat. Off. . |
| 132 880 | 4/1933 | Germany . |
| 3 427 946 | 11/1985 | Germany . |
| 2 227 415 | 8/1990 | United Kingdom . |
| WO 81/03271 | 11/1981 | WIPO . |
| WO-A-85 00280 | 1/1985 | WIPO . |
| WO-A-92 19167 | 11/1992 | WIPO . |
| WO-A-9309839 | 5/1993 | WIPO . |

OTHER PUBLICATIONS

Baumeister, et al, ed., *Mark's Standard Handbook for Mechanical Engineers,* 8th ed, McGraw–Hill Book Co., New York, excerpts pp. 6–42 to 6–46, 1978 (No Month).

Brown et al., "Internal Sclerectomy with an Automated Trephine for Advanced Glaucoma," *Ophthalmology,* vol. 95, No. 6, pp. 728–734 (Jun. 1988).

Brown et al., "Internal Sclerectomy for Glaucoma Filtering Surgery With an Automated Trephine," *Arch Ophthalmol,* vol. 105, pp. 133–136 (Jan. 1987).

(List continued on next page.)

*Primary Examiner*—Marianne Padgett
*Attorney, Agent, or Firm*—Fish & Richardson P.C.

[57] ABSTRACT

An electrosurgical instrument having a first electrode that includes an elongated, electrically conductive member and a second electrode that includes a layer of electrically conductive material adhered over at least a portion of a distal region of the elongated member and separated therefrom by an insulator. The electrodes receive electrical power in a proximal region of the instrument and apply the power to an object in the body by inducing current flow between the electrodes at the distal region. In a related aspect, the second electrode is configured so that the outer diameter of the distal region is substantially the same as the outer diameter of the distal end of the first electrode. In another aspect, one of the electrodes has a reduced circumferential extent relative to the other electrode to limit an area of current flow between the electrodes and thus restrict the size of the region in which cauterization occurs. Still another aspect of the invention features a process for fabricating the electrode assembly.

47 Claims, 5 Drawing Sheets

U.S. PATENT DOCUMENTS

| | | |
|---|---|---|
| 4,483,338 | 11/1984 | Bloom et al. . |
| 4,548,207 | 10/1985 | Reimels . |
| 4,593,691 | 6/1986 | Lindstrom et al. . |
| 4,637,392 | 1/1987 | Sorochenko . |
| 4,686,980 | 8/1987 | Williams et al. . |
| 4,706,667 | 11/1987 | Roos . |
| 4,795,660 | 1/1989 | Cooray et al. . |
| 4,861,624 | 8/1989 | Matsuda et al. . |
| 4,862,890 | 9/1989 | Stasz et al. . |
| 4,876,110 | 10/1989 | Blanch . |
| 4,890,610 | 1/1990 | Kirwan, Sr. et al. . |
| 5,009,656 | 4/1991 | Reimels . |
| 5,318,589 | 6/1994 | Lichtman . |
| 5,336,179 | 8/1994 | Yoon . |

OTHER PUBLICATIONS

Gaasterland et al., "Ab Interno and Ab Externo Filtering Operations by Laser Contact Surgery," *Ophthalmic Surgery*, vol. 18, No. pp. 254–257 (Apr. 1987).

Hasty et al., "Primate Trabeculetomies With 5–Fluoroacil Collagen Implants," *American Journal of Ophthalmology*, 109:721–725 (Jun. 1990).

Higginbotham et al., "Internal Sclerostomy with the Nd:YAG Contact Laser Versus Thermal Sclerostomy in Rabbits," *Ophthalmology*, vol. 95, No. 3, pp. 385–390 (Mar. 1988).

Jaffe et al., "Ab Interno Sclerostomy With a High–Powered Argon Endolaser," *Arch Ophthalmol*, vol. 107, pp. 1183–1185 (Aug. 1898).

Javitt et al., "Laser Sclerostomy ab interno Using a Continuous Wave Nd:YAG Laser," *Ophthalmic Surgery*, vol. 20, No. 8, pp. 552–556 (Aug. 1989).

McGuigan et al., "The Role of Subscleral Schele Procedure in Glaucoma Surgery," *Ophthalmic Surgery*, vol. 17, No. 12, pp. 802–807 (Dec. 1986).

Savage et al., "Coaxial Radio Frequency (RF) Diathermy in Anterior Segment Surgery," *Opthalmic Surgery*, vol. 16, No. 5, pp. 333–336 (May 1985).

The Association Research to Vision and Ophthalmology, Annual Meeting Abstract Issue, Apr.28–May 3, 1991.

Zimmerman et al., AB Interno Filtration Surgery, Dept. of Ophthalmology and Visual Sciences, University of Louisville, Louisville, KY (Abstract Only), Apr./May 1991.

Lee et al., AB Interno Filtration Surgery Part II., Dept. of Ophthalmol and Vis. Sci., Ky., Lions Eye Res. Inst., Univ. of Louisville, Louisville, KY (Abstract Only) Apr./May 1991.

Zimmerman, Thom J., "Let's Turn Glaucoma Filtering Surgery Inside Out," *Clinical Research Forum*, pp. 11–12 No Date.

Sachs et al., "Procedural Options in Cosmetic Blepharoplasty," *Adv. Ohptl Plastics & Reconst. Surgery*, vol. 2, pp. 55–74, 1983. No Month.

Bosniak et al., "Lipolytic Diathermy," *Orbit*, vol. 4, No. ½, pp. 157–160, Feb. 1985.

Bosniak, M.D., F.A.C.S., "Cosmetic Blepharoplasty", 1990, No month pp. 48, 72 73.

DORC, Instrumentation For use with Micro Surgical Systems for Anterior and Posterior Segment Surgery, no date.

"Parylene Coating for Medical Applications". Victor A. Bull No Source or Date Given.

Flynn, Jr., et al. "Cannulated Subretinal Fluid Aspirator for Vitreoretinal Microsurgery", *Americal Journal of Ophthalmology*, vol. 103, No. 1, pp. 106–108, Jan. 1987.

Parel, "A Bipolar Coaxial Microprobe for Safe Transvitreal Diathermy", *Arch Ophthalmol*, vol. 99, pp. 494–497, Mar. 1981.

BIPOLAR ELECTROSURGICAL INSTRUMENT

This is a divisional of copending application Ser. No. 08/591,953, filed Jan. 23, 1996, which is a continuation of application Ser. No. 08/150,925, filed Nov. 10, 1993 now abandoned.

BACKGROUND OF THE INVENTION

This invention relates to bipolar electrosurgical instruments.

Some surgical procedures (such as severe retinal detachment repair and diabetic retinopathy) require the surgeon to insert surgical instruments into the posterior chamber of the eye. Because the eye should be maintained at a relatively constant pressure during the procedure, tubing to which fluid is applied from an elevated (such as by 2–3 feet) irrigation fluid bottle is inserted through the sclera, and the internal eye pressure is controlled by adjusting the height of the bottle.

The need for tightly controlling eye pressure dictates that the surgical instruments be as small as possible in cross-sectional diameter (to minimize leakage around the instruments and limit fluid loss during exchange of the instruments). Accordingly, an informal "standard" has evolved that surgical instruments used in the posterior eye chamber either be made from 20 gauge hypodermic tubing (which is 0.0355 inches in diameter) or be capable of passing through and sealing an opening equivalent to that created by a 20 gauge needle.

Frequent exchanges of the instruments tend to enlarge the puncture and increase fluid leakage, and are also frustrating for the surgeon and time consuming. It thus is desirable to design instruments which can perform multiple tasks. As the complexity of surgical procedures performed in the posterior chamber of the eye increases, the need for additional, intricate instruments increases as well. Basing the size of such instruments on the 20 gauge "standard" severely limits design options. (The need for limiting the size of the bore created by a surgical instrument and minimizing the number of instrument exchanges is not limited to ocular surgery—these goals also exist in other procedures, such as endoscopy and microsurgery on other areas of the body, such as the brain.)

Most extensive posterior surgery requires controlling hemorrhaging, which typically is done using bipolar radio frequency (RF) coagulation. In one coagulation method, two conductive instruments that are otherwise in use in the eye (e.g., an aspiration tube and a metal jacket of a fibre optic light source) are brought close together near the bleeding vessel while applying RF energy to the instruments. Current conducts in the region of closest spacing between the instruments and coagulates the vessel.

As an alternative, coaxial bipolar electrosurgical instruments (such as that described in U.S. Pat. No. 4,548,207, entitled "Disposable Coagulator," assigned to the present assignee and incorporated herein by reference) have been developed. In a coaxial bipolar instrument, an insulated wire is installed within a metal hypodermic tube, thereby providing a pair of electrodes whose distal tips are exposed and closely spaced to support current conduction therebetween. The exposed area limits the extent of the coagulation, which is advantageous in posterior chamber surgery. variations on bipolar instruments include replacing the wire with an inner tube, which allows the instrument to be used for aspiration as well as coagulation.

SUMMARY OF THE INVENTION

This invention provides, in one general aspect, an electrosurgical instrument having a first electrode that includes an elongated, electrically conductive member and a second electrode that includes a layer of electrically conductive material adhered over at least a portion of a the elongated member and separated therefrom by an insulator; a region of the electrically conductive layer is positioned adjacent to a region of the member disposed distally of the proximal end of the instrument to support current flow between the electrodes at the regions and apply electrical power to an object in the body.

In a related aspect of the invention, the second electrode is disposed over at least a portion of the end of the first electrode, is separated therefrom by an insulator, and is configured so that the outer diameter of the distal region is substantially the same as the outer diameter of the end of the first electrode. In a preferred embodiment of this aspect, the second electrode is a layer of electrically conductive material adhered on over the first electrode and separated therefrom by the insulator.

The electrosurgical instrument of the invention is significantly smaller than devices which employ a separate member—such as a tubedisposed coaxially around the first electrode—as the second electrode. One result of this difference is that the dimension of the incision needed for the instrument can be made relatively small, so that a 20 gauge needle may be used for the first electrode, while maintaining the usefulness of the instrument for the dual purposes of coagulation and aspiration. This is particularly important in ophthalmic applications for which (as discussed above) an informal standard has developed that instruments no greater than 20 gauge be used in the posterior chamber of the eye.

Both electrodes are provided in a single instrument that is easily manipulated within the eye. This allows the surgeon to cauterized without performing awkward maneuvers—such as attaching wires from an RF source to a pair of instruments that are to serve as the electrodes, and manipulating the instruments close together with both hands.

Another aspect of the invention is a coaxial electrosurgical instrument one electrode of which has a reduced circumferential extent relative to another electrode to limit an area of current flow between the coaxial electrodes. This limits the size of the region in which cauterization occurs, thereby allowing the user (i.e., a surgeon) to control which body objects are subjected to electrical current more precisely than prior coaxial bipolar instruments in which the exposed distal tips of both electrodes are circular. As a result, damage to sensitive tissue (such as structures of the eye) can be avoided by appropriately directing the current away from these objects.

Preferred embodiments of one or more of these aspects of the invention include the following features.

The insulator is disposed over an exterior surface of the first electrode, and the layer of conductive material of the second electrode is adhered to the insulator and extends axially along the first electrode between the proximal end and the distally disposed region. The distally disposed region is preferably near the distal end of the instrument. The conductive layer is separated from the exterior surface of the first electrode by an insulator (such as a layer of plastic). The outer diameter of the first electrode is on the order of 20 gauge; by contrast, the thickness of the layer of conductive material is on the order of 3–5 microns (i.e., between 0.001 inches and 0.002 inches. Thus, the second electrode does not significantly add to the size of the first electrode. If desired, a second layer of insulation can be disposed over at least the layer of electrically conductive material for protection during handling.

The layer of conductive material extends over one half or less of the circumference of the first electrode, such as between one-third and one-half of the circumference, at least in the distal region. In a particularly useful example of this configuration, the first electrode is a hollow tube and the layer of conductive material is configured as an elongated strip that runs along the length of the tube between the proximal end and the distal region.

The tip of the tube at the distal region has a limited circumferential extent with respect to other portions of the tube, and the layer of electrically conductive material is circumferentially aligned with the tip. This provides even greater control over the areas to which the cauterizing current is applied. In one configuration, the circumferential extent of the layer is less than that of the tip. The distal region of the tube is beveled to provide the tip. The bevel affords the surgeon with an unobstructed view of the tip during cauterization. The tip includes a surface disposed transversely to the longitudinal axis of the instrument—that is, the tip of the bevel is blunt rather than sharp. A blunt tip helps avoid damage to tissue contacted by the instrument during operation.

In another embodiment, the layer of conductive material is disposed completely around the perimeter of the exterior surface in the distal region. Although the area to which current is applied is circumferential, this configuration is particularly useful in cauterizing incisions. In one example of this embodiment, the member is a cutting blade, and the distal end of the layer is disposed completely around a wide region of the blade proximally of the region of the blade that narrows to the tip. An incision cut by the blade is cauterized completely around its perimeter by advancing the blade to place the distal end of the layer adjacent to the incision while applying the bipolar power to instrument to induce current flow between the blade and the layer.

In embodiments in which the member (i.e., the inner electrode) is a hollow tube, the tube is sized to provide an interior passage that is sufficiently large to slidably receive a device during use and allow the device to be advanced to at least the distal region of the tube. A 20 gauge needle is well suited for this purpose. Examples of such devices include an aspiration tube and a fibre optic cable. The interior passage (i.e., the bore) of a 20 gauge needle is sufficiently large so that such devices can be freely advanced and retracted therethrough without binding. Because the outer electrode is a layer of conductive material adhered to the exterior of the needle—rather than a smaller needle coaxially disposed within the 20 gauge needle—the entire diameter of the passage is available to receive the device. As a result, the risk of the device binding during use is significantly reduced.

Another aspect of the invention is a process for fabricating an electrosurgical instrument by providing a first electrode that includes an elongated, electrically conductive member, disposing an insulating material over at least a portion of a surface of the member, and forming a layer of electrically conductive material over the insulating material to provide a second electrode.

Preferred embodiments include the following features.

The layer is formed in any of the configurations discussed above—for example, in the shape of an elongated strip that extends between the proximal end and the distal region of the member, or completely around the circumference of the member.

The electrically conductive material is made from silver and is formed by vapor deposition. The silver layer is deposited to a thickness of between 3 microns and 5 microns. Materials other than silver (such as nickel, gold, palladium, platinum, tin, etc.) may alternatively be used. In addition, a second layer of conductive material may be deposited over the first layer of conductive material. This is particularly useful when silver or another material that tarnishes is used as the first layer of conductive material. Depositing a suitable metal (such as gold) over the silver avoids tarnishing.

Preferably, a sub-layer of electrically conductive material is applied over the insulating material before the layer of electrically conductive material of the second electrode is deposited. The sub-layer (which is, for example, titanium) serves as a primer to improve the adhesion of the silver or nickel. The insulating material preferably comprises a conformal insulating layer, such as a polymer (for example, parylene).

The bipolar electrosurgical instrument of the invention has a variety of applications in addition to coagulation. For example, the instrument is useful in intraocular diathermy to mark retinal breaks and assist the surgeon in locating the breaks as air enters the eye during fluid/gas exchange. Also, the aspiration tube that extends through the first electrode can be used as a brush to manipulate large retinal tears and to assist the surgeon in assessing the strength of vitreous strands near (and on) the retina. The amount by which the tube can be extended beyond the tip of the electrode determines the rigidity of the "brush."

Moreover, the aspiration tube allows pre-retinal blood or fluids so often encountered with proliferative diabetic retinopathy to be passively or actively aspirated from the eye. A drainage retinotomy can be achieved by cauterizing a spot on the retina, thinning the targeted tissue, and then applying suction via the extended tube. Subsequent extension of the aspiration tube through the retinotomy (or through a peripheral retinal break in eyes that have complex retinal detachments) achieves drainage of sub-retinal fluid (and hemorrhages). Likewise, the profile of bullous retinal detachments can be reduced at the start of vitreoretinal procedures in order to facilitate access to pre-retinal membranes.

Bubbles of air, gas, or silicone oil droplets which become trapped beneath the retina, or floating anterior, may be removed using active or passive aspiration with the tube extended through the first electrode. Moreover, the extended tube may be used for reflux.

Other features and advantages of the invention will become apparent from the following detailed description, and from the claims.

DESCRIPTION OF THE PREFERRED EMBODIMENTS

Referring to FIGS. 1–5, an electrode assembly 10 of a bipolar electrosurgical instrument includes one electrode 12 made from a stainless steel, 20 gauge hollow needle and a second electrode 14 formed as a layer of electrically conductive material (such as silver or nickel) deposited over and adhered on an exterior surface 16 of needle electrode 12. A thin electrical insulator 15 separates electrodes 12, 14 along their lengths to avoid short circuiting.

Electrodes 12, 14 extend coaxially along a longitudinal axis 18 of the instrument from a proximal region at which bipolar electrical power is applied (from a source not shown) to a distal region 20 of electrode assembly 10. As explained in more detail below, tips 22, 24 (FIG. 5) of electrodes 12, 14 are closely spaced in distal region 20 so that when the instrument is energized, current flow is induced between electrode tips 22, 24 through an object in the body (such as a blood vessel or tissue within the eye) to perform cauterization and other procedures (such as tissue shrinking).

Electrode 14 extends over a limited portion of the circumference of electrode 12, rather than entirely around electrode 12. Moreover, as discussed below, electrode 12 is configured so to have a narrow tip 22 that is exposed to tip 24 of electrode 14 only at a face 23 at a distal tip 21 of the instrument. As a result, current flow between electrodes 12, 14 occurs over only the width W (e.g., 0.01 inches) of tip 22. It will thus be appreciated that current flow occurs over a relatively small portion of the circumference of electrode 12. This limits the area in the body that receives current, and provides the user (e.g., a surgeon) with a high degree of control as to where the current is applied. This is particularly advantageous in eye surgery, during which the electrodes are often used to cauterize bleeding blood vessels near sensitive tissue that may be damaged if subjected to electrical current.

Figure 1:
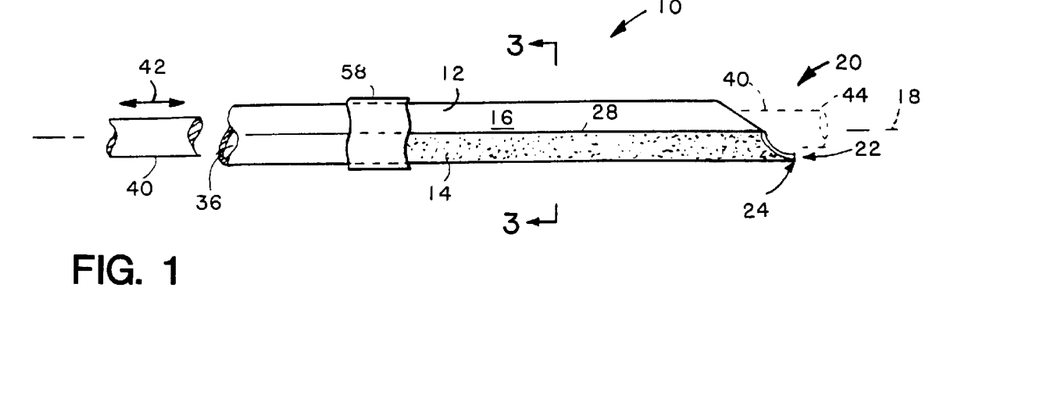
FIG. 1 diagrammatically shows a portion of an electrosurgical instrument according to the invention, in which one electrode is configured as a layer of electrically conductive material adhered on a metal tube, which serves as the other electrode of the instrument.
Figure 2:
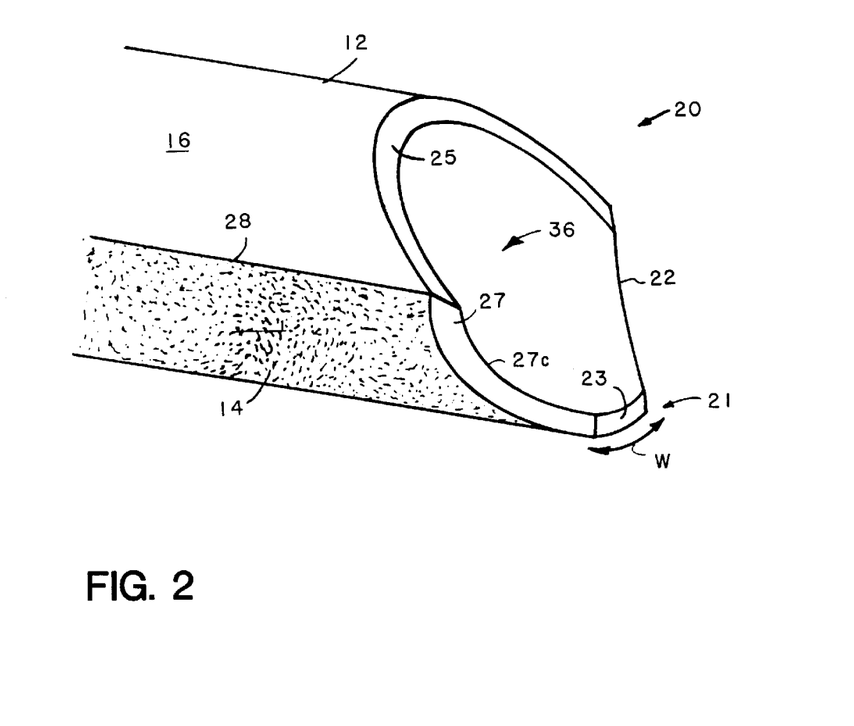
FIG. 2 is a perspective view of the surgical instrument of FIG. 1.
Figure 3:
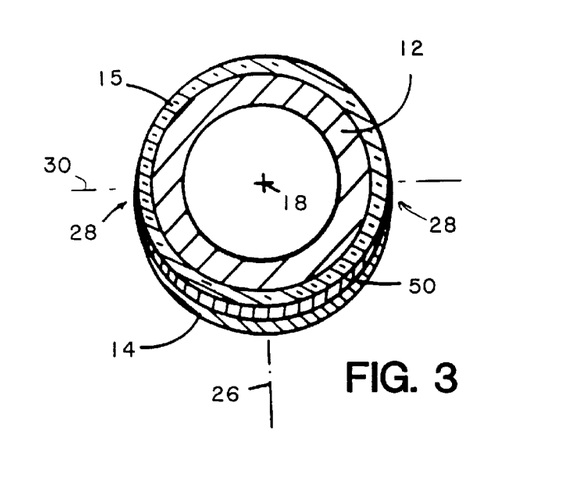
FIG. 3 shows a cross section of the surgical instrument of FIG. 1, taken along line 3—3.

As shown in FIG. 3, electrode 14 extends over an arc of approximately one half of the circumference of electrode 12, such as between ⅜ and ⅝ of the circumference. Electrode 14 is disposed symmetrically about an axis 26 that vertically bisects electrode 12 and terminates circumferentially in edges 28 that lie approximately on an axis 30 that horizontally bisects electrode 12. As discussed below, electrode 14 is formed by vacuum deposition, and thus the thickness of electrode 14 decreases from a maximum (such as 5 microns) at vertical axis 26 to zero as electrode 14 extends circumferentially toward axis 30. (Thus, edges 28 are "feathered" rather than being sharply defined.)

Figure 4:
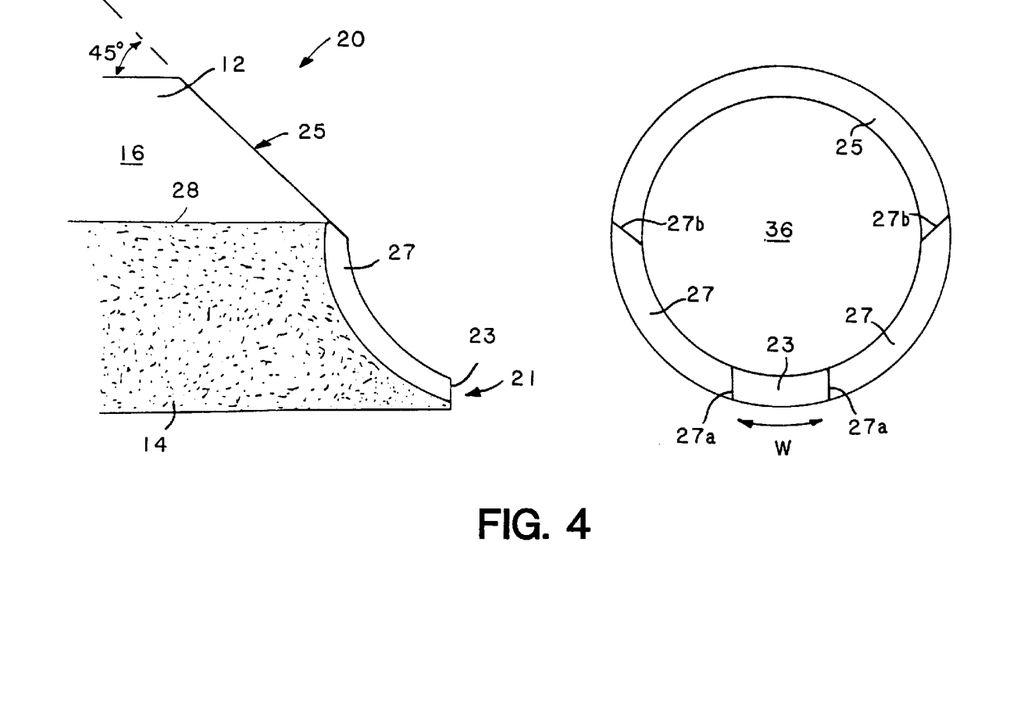
FIG. 4 shows enlarged views of the distal region of the surgical instrument of FIG. 1 from the side and tip.
Figure 5:
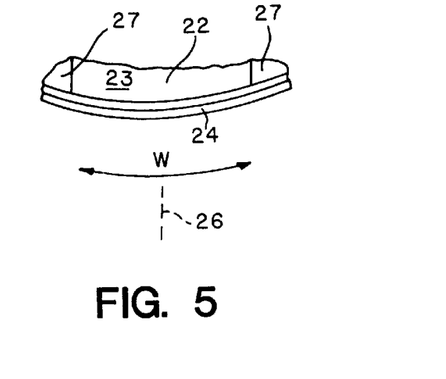
FIG. 5 shows a greatly enlarged view of a portion of the tip of the surgical instrument of FIG. 1.

As shown in FIG. 4, distal region 20 is beveled to form a surface 25 oriented at an oblique angle (e.g., 45°) with respect to longitudinal axis 18. In addition, a pair of beveled surfaces 27 are formed in the half of electrode 12 on which electrode 14 is disposed (i.e., the lower half in the figures). Beveled surfaces 27 are oriented at an angle of 90° to each other and converge to form tip 21 at the extreme distal end of the instrument. Beveled surfaces 27 join with beveled surface 25 at edges 27b. Bevels 25, 27 are formed by a grinding process discussed below. Tip 21 is subsequently ground flat to form face 23, which is oriented perpendicularly to longitudinal axis 18 and is symmetrically disposed with respect to axis 26. Face 23 meets the beveled surfaces 27 at edges 27a. Electrode tips 22, 24 are coextensive at face 23. Thus, tip 21 is blunt, rather than sharp. The blunt nature of tip 21 helps avoid inadvertent damage to sensitive eye tissue during the surgical procedure.

Electrode 12 has a central passage 36 that is open at distal region 20. Because electrode 14 is adhered to exterior surface 16 of electrode 12, the entire diameter of passage 36 (which, for a 20 gauge needle, is 0.0305 inches) is available to slidably receive a device 40 used in conjunction with the instrument during surgery. Examples of device 40 are a hollow tube for aspirating irrigation fluid and other liquids from the eye, and a fibre optic cable for illuminating the surgical site (the site is viewed through the cornea with a microscope, not shown). Passage 36 of a 20 gauge needle is sufficiently large to allow such devices 40 to be advanced and retracted (in the direction of arrow 42) through electrode 12 without binding. Device 40 can be advanced so that its distal end 44 (shown in phantom in FIG. 1) extends distally beyond distal region 20, or not.

Figure 6:
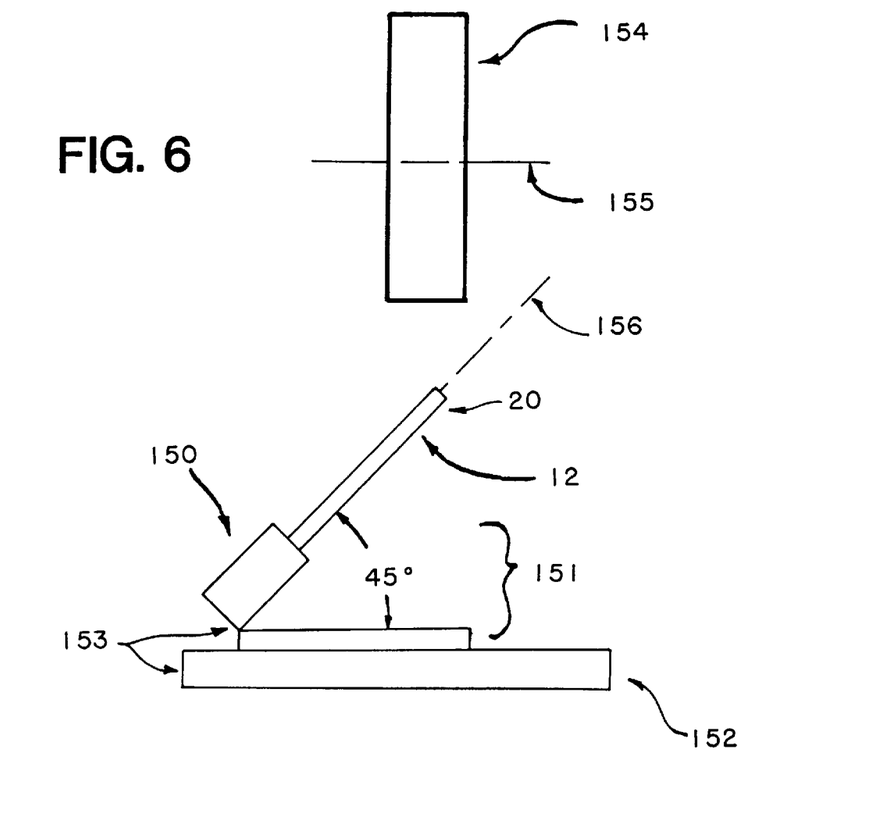
FIG. 6 shows an assembly for bevelling the tip of the surgical instrument of FIG. 1.

Referring to FIG. 6, the first step in fabricating electrode assembly 10 is to grind distal region 20 to form beveled surfaces 25, 27. Electrode 12 is placed in a collet-type indexing fixture 150, which is mounted on a sine plate 151 set at 45° to a mounting table 152 of a surface grinder. Pivot axis 153 of sine plate 151 is parallel to the direction of longitudinal travel of mounting table 152 (into and out of the page in FIG. 6). Grinding wheel 154 rotates about an axis 155 that is perpendicular to the direction of longitudinal travel of mounting table 152. Pivot axis 156 of indexing fixture 150 is perpendicular to pivot axis 153 of sine plate 151.

The complete cross section of electrode distal region 20 is ground at 45° with indexing fixture 150 set at 0°. This forms beveled surface 25 over the entire diameter of electrode 12. Grinding wheel 154 is then retracted and electrode 12 is rotated by indexing fixture 150 to a setting of +90°, and grinding wheel 154 is brought back into contact with electrode 12. Grinding wheel 154 is again retracted, and electrode 12 is rotated by indexing fixture 150 to a setting of +90°; grinding wheel 154 is then brought back into contact with electrode 12. The grinding procedure is repeated at the +90° and −90° fixture settings, with grinding wheel 154 lowered slightly during each repetition, until a point is formed at tip 21. Sharp edges and burrs are removed manually, e.g., using hard Arkansas stones and hand scrapers (hand honing and scraping can be eliminated by grinding electrode 12 using an electrochemical grinding process, or ECG).

Referring again to FIG. 2 and FIG. 3 (which shows the thicknesses of the various layers applied over electrode 12 greatly exaggerated for purposes of illustration), insulating layer 15 is formed on electrode 12 after grinding. Insulating layer 15 is made from Parylene C, a polymer commercially available from Union Carbide Corporation, and is applied by any suitable method, such as vapor deposition. During vapor deposition, a granular powder that comprises the insulating material is vaporized at an elevated temperature, and the resulting gas is deposited on electrode 12 in an ambient temperature deposition chamber (not shown). The insulating material is adsorbed on exterior surface 16 of electrode 12 as it polymerizes thereon, and also forms on tip 21 (which is a sharp point at this stage), and beveled surfaces 25, 27; some insulating material is also deposited on the interior surface of electrode 12.

Insulating layer 15 should be as thin as possible (for ease of fabrication and to keep electrode assembly 10 small), while serving its purpose of electrically insulating electrodes 12, 14 from each other. The total thickness of insulating layer 15 is between 0.0008 inches and 0.001 inches and thus adds insignificantly to the outer diameter of electrode 12 (which for a 20 gauge needle is 0.0355 inches). The proximal end of electrode 12 is masked to form a window (not shown) in insulating layer 15. The window provides an electrical contact point for a wire that delivers electrical current to electrode 12.

A layer 50 of titanium is then applied by ion vapor deposition in a high vacuum on insulating layer 15 over the portions of electrode 12 that will be covered by electrode 14. Thus, layer 50 is applied along the length of electrode 12 and extends over a limited portion (such as approximately 180°) of the circumference of electrode 12. Electrode 12 is masked to limit the portions of insulating layer 15 that are covered by the titanium. This process is discussed in more detail below with respect to the formation of electrode 14. Titanium adheres well to the insulating material of layer 15, and thus serves as a primer to improve the adherence of electrode 14. Layer 50 need not be very thick (e.g., less than 1 micron, or 0.00004 inches) to serve this purpose.

Figure 7:
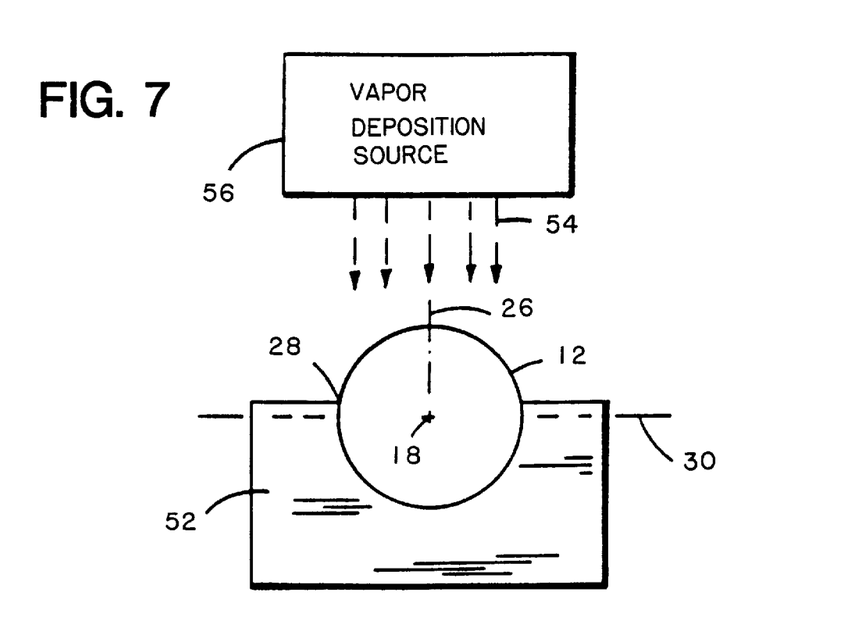
FIG. 7 illustrates forming the electrode layer by vapor deposition.

Referring also to FIG. 7, electrode 14 is then formed over titanium layer 50 by ion vapor deposition in a high vacuum. Silver has been found to be a suitable material for electrode 14 for several reasons. Silver is a good conductor of electricity, and it is also more compatible with the sensitive tissue of the eye than other metals (such as copper). In addition, silver is relatively soft and does not impose large stresses on underlying titanium layer 50 during deposition. A mask 52 shields portions of electrode 12 that are not to be covered by electrode 14 from the silver ions 54 emitted by a vapor deposition source 56. Mask 52 also covers the portions of electrode 12 disposed below electrode edges 28 (with respect to horizontal axis 30).

As will be appreciated from FIG. 7, silver ions 54 are deposited symmetrically with respect to vertical axis 26 so that the thickness of electrode 14 is greatest near axis 26 and tapers smoothly toward edges 28. Electrode 14 can be laid down to any suitable thickness such as between three microns and five microns, but electrode 14 should be sufficiently thick to conduct the level of current used during the operation of the instrument (which is typically 30 milliamperes). A thickness of 5 microns (i.e., 0.0002 inches) at vertical axis 26 has been found to work well under these conditions. The thickness decreases somewhat linearly as electrode 14 extends circumferentially toward edges 28. Silver ions 54 may also be deposited on beveled surfaces 25, 27. Because some insulation 15 is formed on the inner surfaces of electrode 12, no cauterization occurs edges 27c (FIG. 2) of beveled surfaces 27.

Next, a clear plastic layer 58 (FIG. 1) is optionally formed over electrodes 12, 14. (Layer 58 is omitted from FIG. 3 for clarity.) Layer 58 helps protect electrodes 12, 14 from damage during handling and also serves as an insulating sheath for electrode 14 (and thus may be necessary in some surgical applications). Layer 58 is relatively thin (e.g., 0.0005 inches) and is made from Teflone®, although layer 58 need not be as rugged as the material used for insulating layer 15. Layer 58 ends slightly distally of the proximal end of electrode 14 so that electrical contact can be made to electrode 14 at the proximal end.

Referring again to FIG. 2 and 5, after electrodes 12, 14 have been formed, the sharp point at tip 21 is honed perpendicularly to tube axis 18 using a hard Arkansas stone to form flat, relatively wide face 23. Honing continues until the desired width (W) of 0.01 inches (25 mm) of face 23 is obtained. In addition to flattening tip 21, the honing process also exposes tip 22 of electrode 12 and tip 24 of electrode 14. As a result, the width of coagulation of the instrument is determined by width W of face 23. Electrode assembly 10 is now ready to be mounted within the electrosurgical instrument.

Figure 8:
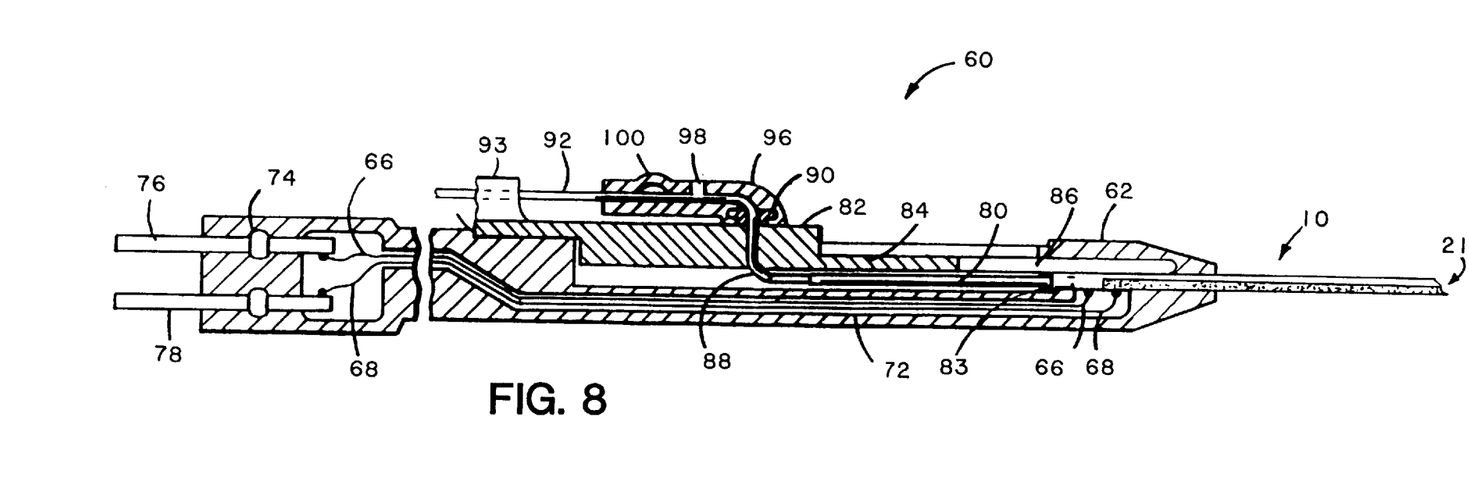
FIGS. 8 and 9 are cross-sectional views showing additional features of the electrosurgical instrument of FIG. 1.

Referring to FIG. 8, electrosurgical instrument 60 provides a plastic housing 62 for electrode assembly 10, as well as wiring for applying the bipolar energizing potential to electrodes 12, 14. Electrode assembly 10 rests in a cavity at the distal end 64 of housing 62. Distal end 64 is tapered for ease of use. A pair of wires 66, 68 are soldered to the proximal ends of electrodes 12, 14. Wires 66, 68 extend through a channel 72 in housing 62 and are soldered to a pair of pins 76, 78 at the proximal end 74 of housing 66. Pins 76, 78 serve as a plug to receive the bipolar energizing potential.

A silicone plastic aspiration tube 80 (i.e., one of the devices 40 discussed above in connection with FIG. 1) is selectively advanced and retracted within electrode assembly 10 through passage 36 by an actuator 82 that is mounted to slide with respect to housing 62. Specifically, a forward tongue 84 of actuator 82 slides within an elongated slot 86 in housing 62. A section 83 of TFE shrink tubing is disposed around the proximal end of electrode 12 and extends slightly proximally thereof. Tubing section 83 fits snugly around aspiration tube 80 and thus serves as a seal to help prevent fluid captured between electrode 12 and tube 80 from leaking into housing 62.

A hollow metal pipe 88 is rigidly mounted to actuator 82 and is snugly received within the interior bore of aspiration tube 80 (which is 0.012 inches in diameter). Pipe 88 extends almost completely through aspiration tube 80 and provides added rigidity to help tube 80 slide smoothly within passage 36. Pipe 88 is sufficiently long so that it remains within the proximal end of passage 36 even when actuator 82 is in the fully retracted position shown in FIG. 8. This helps avoid binding of aspiration tube 80 when actuator 82 is advanced. Pipe 88 terminates slightly proximally of the distal end of aspiration tube 80 (FIG. 9) to ensure that aspiration tube 80 does not become accidentally dislodged from electrode 12 and cast loose within the eye.

Figure 10:
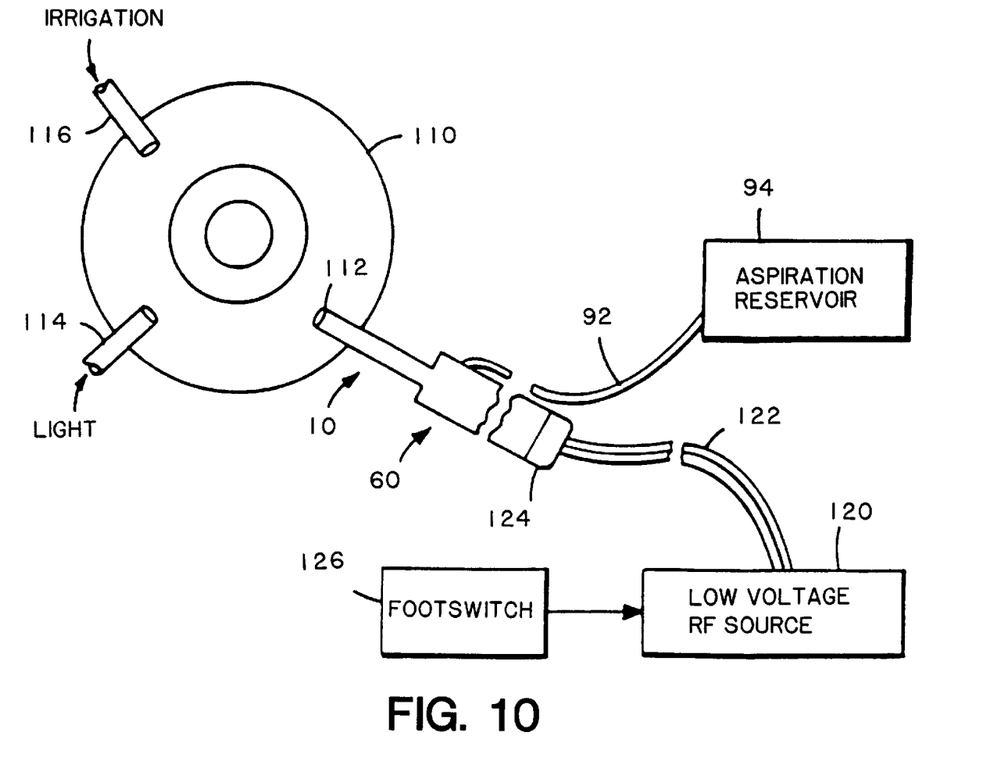
FIG. 10 illustrates the electrosurgical instrument of FIG. 1 in use.

Pipe 88 extends upwardly through actuator 82 to a post 90, where pipe 88 is joined to an external tube 92 that passes rearwardly through a tunnel 93 on housing 62 to drain the aspirated fluid into a reservoir 94 (FIG. 10). A hood 96 secured to tube 92 fits snugly over post 90 and includes an aperture 98 that serves as a valve to allow the surgeon to regulate aspiration by selectively covering and uncovering aperture 98 with the finger. An enlarged bump 100 that can be felt through a surgical glove is positioned slightly behind aperture 98 to assist the surgeon in locating aperture 98 by feel. The surgeon can shut off aspiration by depressing bump 100 slightly; depressing bump 100 still further causes reflux to be applied through pipe 88 from a fluid reservoir (not shown) in housing 62. (Alternatively, a plug, not shown, may be inserted in aperture 98 if the surgeon prefers not to use his or her finger.)

Figure 9:
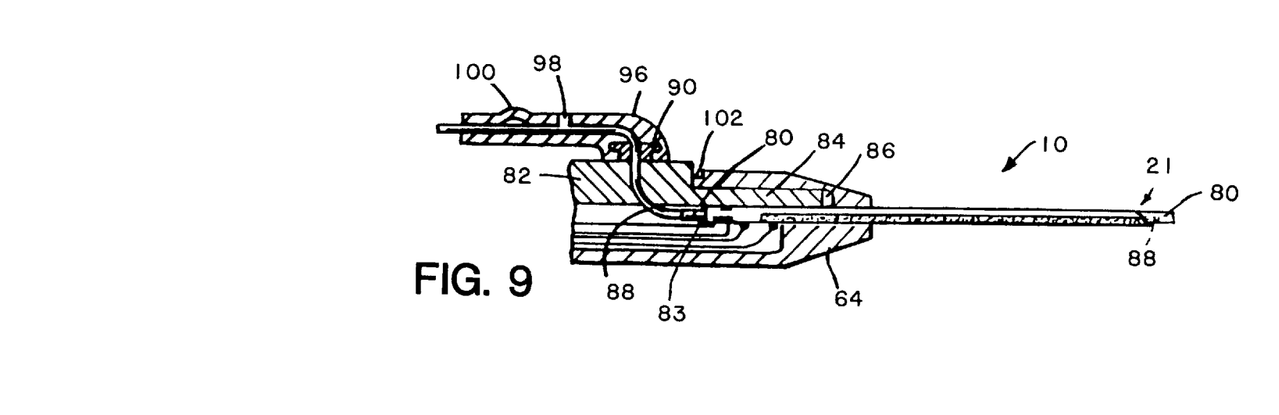

Referring also to FIG. 9, the surgeon advances aspiration tube 80 through passage 36 simply by sliding actuator 82 (e.g., using the index finger of the hand) toward distal end 64 of housing 62 in slot 86. A shoulder 102 on housing 62 limits the forward travel of actuator 82. With actuator 82 positioned as shown in FIG. 9, the distal end of aspiration tube 80 extends beyond tip 21 of electrode assembly 10. This allows the surgeon to maintain electrode assembly 10 spaced away from the area of the eye being aspirated by tube 80, if desired. The surgeon retracts tube 80 from the surgical site into passage 36 by sliding actuator 82 rearwardly. A shoulder 104 on housing 62 (FIG. 8) limits the travel of actuator 82 to avoid withdrawing tube 80 from the proximal end of electrode 12.

Referring to FIG. 10, in operation during ophthalmic surgery, electrode assembly 10 is inserted into the eye 110 through a small incision 112 in the sclera. Light is applied through a trocar 114 inserted through a second incision, and irrigating fluid is introduced through tube 116 inserted through a third incision.

Because electrode 14 is formed as a layer adhered on electrode 12—rather than as a separate metal tube coaxially disposed around electrode 12—the outer diameter of electrode assembly 10 is substantially the same as that of electrode 12. For example, with a 20 gauge needle (which has an outer diameter of 0.0355 inches) used for electrode 12, the outer diameter of electrode assembly 10 (with layers 14, 15, and 50 having the thicknesses discussed above) is only 0.0024 inches. As a result, incision 112 need be only slightly larger than that needed for a 20 gauge needle, thereby minimizing eye trauma.

Moreover, disposing electrode 14 over exterior surface 16 of electrode 12 leaves the entire interior diameter of passage 36 open to receive aspiration tube 80. This is a distinct improvement over previous bipolar instruments that used a 20 gauge needle as the outer electrode and a smaller size needle (e.g., 25 gauge) within the outer needle as the second electrode, thereby sacrificing a portion of the diameter of the passage through the 20 gauge needle.

Instrument 60 is connected to a low voltage RF power source 120 via a power cord 122 and a socket 124 that mates with pins 76, 78 (FIG. 8) on housing 62. Low voltage RF source 120 is a Wet-Field® II Coagulator commercially available from Mentor O & O Inc., of Norwell, Mass. RF source 120 produces a relatively low bipolar output voltage (e.g., approximately 90 volts RMS under no-load conditions). A low voltage source 120 is preferred to avoid arcing between electrode tips 22, 24 which could damage the eye tissue.

Instrument 60 is advantageously used to cauterize bleeding blood vessels during ophthalmic surgery in the posterior chamber of the eye. The surgeon manipulates instrument 60 to place tip 21 against the bleeding vessel, and then performs cauterization by activating power source 120 with footswitch 126. The RF power level applied to electrodes 12, 14 is adjusted using, for example, controls (not shown) on the front panel of source 120. Current flow is induced through the area of the eye adjacent to the vessel between closely spaced electrode tips 22, 24, thereby cauterizing the vessel and stopping the hemorrhaging.

The beveled configuration of distal region 20 and the alignment of electrode 14 with tip 21 provides several advantages. For one, this configuration ensures that electrodes 12, 14 have closely spaced, exposed surfaces only at tips 22, 24—that is, at distal tip 21 of the instrument. As a result, cauterizing current is highly focused within an area defined by width W of tip 21. Moreover, the thickness of the silver is greatest at tip 21, thereby helping to ensure that electrode 14 will support the current levels needed during surgery. Put another way, current flow is highly localized with respect to the circumference of electrode 12. This allows the surgeon to precisely control the area in the eye to which the cauterizing current is applied by controlling the position of tip 21 (which, because it protrudes beyond the remainder of distal region 20, is easy to observe). Moreover, because beveled tip 21 is positioned on the underside of assembly 10 (as shown in, for example, FIG. 8) so that beveled edges 25, 27 face the surgeon through eye 110, tip 21 is left unobscured. This enables the surgeon to clearly visualize progress of the cauterization.

Other Embodiments

Other embodiments are within the scope of the following claims.

For example, electrodes 12, 14 can have many other configurations. One alternative is to expose electrodes 12, 14 to each other in regions other than tip 21. For example, one or more regions of layer 14 and underlying areas of insulator 15 may be removed (e.g., by filing) at any suitable location along axis 18 to expose electrodes 12, 14 to one another. Cauterization would occur in these regions.

The circumferential extent of electrode 14 can be further limited (e.g., to one-sixth of the circumference of electrode 12 or less), depending upon the degree of control desired over the size of the area to which current is applied. Alternatively, electrode 14 can extend around a greater portion of the circumference of electrode 12 in distal region 20 (or along other portions of the length of electrode 12). If electrode 14 is disposed completely around electrode 12 in distal region 20, the cauterization pattern will be annular.

Still other configurations of electrode 14 are possible. For example, multiple, circumferentially spaced strips may be provided in place of the single strip shown in FIG. 1. This would allow cauterization to occur at discrete locations around the periphery of electrode 12.

Face 23 need not be perpendicular to the sides of electrode 12. Instead, a portion (or all) of face 23 may be beveled, either in the same direction as bevels 25, 27, or in a retrograde manner. Beveling face 23 will, of course, affect the location of cauterization at tip 21.

Electrode 12 need not have both bevels 25, 27. Either may be used alone, or no beveling may be provided. If electrode 12 is not beveled and electrode 14 is formed completely around the circumference of electrode 12 at tips 22, 24, current flow would be present around the entire perimeter of electrode 12. This may be desirable in some applications and is certainly contemplated by the invention.

Electrode assembly 10 may have still other configurations. For example, electrode 12 need not be a 20 gauge needle, or a needle of any kind. Electrode 12 may be solid rather than hollow.

Figure 11:
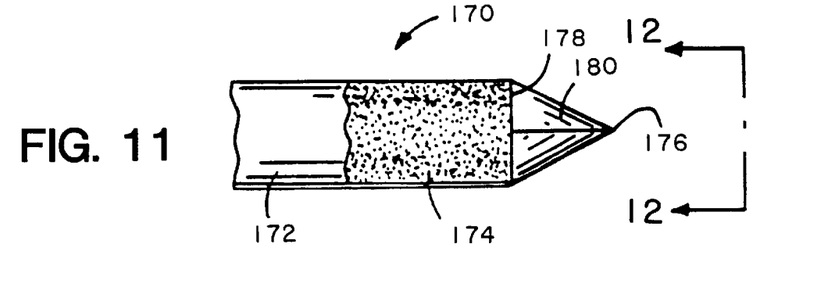
FIGS. 11 and 12 show an alternative configurations the electrodes according to the invention.
Figure 12:
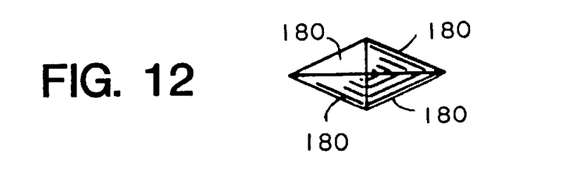

For example, referring to FIGS. 11 and 12, electrode assembly 170 is a cauterizing knife in which the inner electrode is a solid, stainless steel blade 172 that is coated over most of its length with metal layer 174 (which serves as the second electrode). Metal layer 174 terminates proximally of the sharp tip 176 of blade 172. More specifically, the distal end of metal layer 174 is coextensive with a diamond-shaped region 178 at which blade 172 begins to narrow from a relatively large diameter to tip 176 in four beveled surfaces 180.

During operation, tip 176 is used to cut an incision, for example, through the sclera of eye 110 (FIG. 10). As blade 172 is advanced slightly further into the eye, power source 120 (FIG. 10) is activated, and the incision is completely cauterized by current flow between layers 172, 174 in wide region 178. Thus, a relatively large, cauterized incision is quickly made.

In all of the embodiments discussed above, the insulator that separates the electrodes (e.g., layer 15, FIG. 3) need only be disposed over the portions of the inner electrode (e.g., electrode 12) that are covered by the outer electrode (e.g., electrode 14). Likewise, if outer insulating layer (e.g., layer 58, FIG. 1) is used, it can be disposed only over the outer electrode, if desired. The titanium primer (e.g., layer 50, FIG. 3) can alternatively extend around the entire circumference of the inner electrode, even if the outer electrode has a limited circumferential extent.

Mask 52 need not be used during the deposition of electrode 14. Instead, electrode 12 may simply be laid on a flat surface during deposition of electrically conductive layer 14.

Alternative materials may be used for electrodes 12, 14. For example, electrode 14 may be made from nickel, gold, palladium, platinum, tin, etc. Copper may also be used, particularly if outer insulating layer 58 is employed. Even if layer 58 is not provided, the use of copper may not be detrimental, given the short periods of time that electrode assembly 10 is typically in place in the eye. If silver is used for electrode 14, an additional metal layer (such as gold) may be deposited thereon to avoid tarnishing.

Other suitable insulators may be used. One possible substitute is teflon. Insulating layer 58 may be even more desirable if a relatively hard metal (such as nickel) is used for electrode 14 and teflon is used for insulating layer 15.

The bipolar electrosurgical instrument of the invention can be reusable or disposable.

Still other embodiments are within the scope of the claims.

What is claimed is:

1. An electrosurgical instrument comprising
   a first electrode including an electrically conductive tube having a proximal region for receiving electrical power and a passage extending through said tube to an opening at a distal region,
   a film of insulating material disposed on a portion of a surface of said tube between said proximal region and said distal region, and
   a second electrode including a film of electrically conductive material disposed over said film of insulating material less than completely around a circumference of said tube and having a tapered thickness from a central circumferential portion thereof toward a circumferential edge thereof, said film of electrically conductive material having a proximal region for receiving the electrical power and a distal region positioned adjacent to said distal region of said tube and spaced therefrom by said film of insulating material, thereby to support electrical current flow between said electrodes at said distal regions in response to the received electrical power.

2. The instrument of claim 1 wherein said tube has a distal tip at said distal region, said film of conductive material having a distal end disposed proximally of said distal tip.

3. The instrument of claim 1 wherein said tube has a distal tip in said distal region, said distal tip having a limited circumferential extent with respect to other portions of said distal region, said distal region of said film of electrically conductive material being circumferentially aligned with said tip.

4. The instrument of claim 3, wherein said region of said film of electrically conductive material has a circumferential extent that equals the circumferential extent of said tip.

5. The instrument of claim 3 wherein said distal region of said tube is beveled to provide said tip.

6. The instrument of claim 3 wherein said tip includes a surface disposed transversely to a longitudinal axis of said instrument.

7. The instrument of claim 1 wherein said passage is configured to receive a device during use of said instrument.

8. The instrument of claim 7 wherein said device includes an aspiration tube, said passage and said aspiration tube being sized to allow said aspiration tube to be advanced to at least said opening at said distal region of said tube to remove fluid from a surgical site and thereafter retracted from said distal region.

9. The instrument of claim 8 wherein said tube comprises a 20 gauge needle.

10. The instrument of claim 8 wherein said device includes a fibre optic cable.

11. The instrument of claim 1 wherein said film of insulating material includes a polymer.

12. The instrument of claim 1 wherein said film of electrically conductive material is adhered to said film of insulating material.

13. The instrument of claim 1 further comprising a surgical device disposed in said passage so that a distal end of said surgical device is disposed at said opening.

14. The instrument of claim 13 wherein said surgical device is an aspiration tube.

15. The instrument of claim 13 wherein said surgical device is a fibre optic cable.

16. The instrument of claim 13 wherein said tube and said passage are sized for selective movement of said surgical device within said tube so that said distal end of said surgical device can be selectively advanced and retracted with respect to said opening.

17. The instrument of claim 1 further comprising
   a housing to which said proximal region of said tube is attached, said housing having an electrical connector with a pair of electrical contacts,
   a first one of said contacts being connected to said proximal region of said tube, and a second one of said contacts being connected to said film of electrically conductive material, said contacts being configured to receive energy from a source to cause said tube and said film of electrically conductive material to carry electrical current and induce current flow between said distal regions.

18. The instrument of claim 17 wherein said tube is a needle.

19. The instrument of claim 1 or 17 wherein said film of insulating material is disposed less than completely around the circumference of said tube.

20. The instrument of claim 1 wherein said film of conductive material is disposed over between ⅓ and ½ of said circumference of said tube.

21. The instrument of claim 1 or 17 wherein said film of insulating material is disposed completely around the circumference of said tube.

22. The instrument of claim 1 or 17 wherein said film of electrically conductive material is configured as an elongated strip of said electrically conductive material and extends between said proximal region and said distal region of said tube.

23. The instrument of claim 22 wherein said strip is disposed over between ⅓ and ½ of the circumference of said tube at least at said distal region.

24. The instrument of claim 19 further comprising an outer layer disposed over at least said film of electrically conductive material.

25. The instrument of claim 19 wherein said distal region of said film of conductive material is disposed over less than one half of a circumference of said tube.

26. And electrosurgical instrument comprising
a first electrode including an electrically conductive needle having a diameter of a selected gauge suitable for insertion into an eye to perform surgery thereon and configured to carry electrical current between a proximal region and a distal region,
a film of insulating material disposed on a portion of a surface of said needle between said proximal region and said distal region of said needle, and
a second electrode including a film of electrically conductive material disposed over said film of insulating material so that a distal region of said film of electrically conductive material is positioned adjacent to said distal region of said needle and is spaced therefrom by said film of insulating material, said film of insulting material and said film of electrically conductive material having thicknesses such that the diameter of said needle with said films disposed thereon is substantially said selected gauge.

27. The instrument of claim 26 wherein said diameter is on the order of 20 gauge, said film of insulating material has a thickness of 0.001 inch or less, and said film of electrically conductive material has a thickness of 5 microns or less.

28. The instrument of claim 26 wherein said needle is hollow.

29. The instrument of claim 1 or 26 wherein said film of electrically conductive material is a vapor deposition layer.

30. The instrument of claim 29 further comprising a sub-layer of electrically conductive material disposed between said film of insulating material and said film of electrically conductive material.

31. The instrument of claim 30 wherein said insulating material comprises a polymer, said sub-layer comprises titanium, and said electrically conductive material comprises gold.

32. The instrument of claim 1 or 26 wherein said film of insulating material comprises a conformal insulating layer.

33. The instrument of claim 1 or 26 wherein said film of insulating material comprises parylene.

34. The instrument of claim 1 or 26 wherein said film of insulating material has a thickness of 0.001 inch or less, and said film of electrically conductive material has a thickness of 5 microns or less.

35. The instrument of claim 1 or 26 wherein said electrically conductive material comprises silver, nickel, gold, palladium, platinum, or tin.

36. The instrument of claim 1 or 26 further comprising a layer of electrically conductive material disposed over said film of electrically conductive material.

37. The instrument of claim 26 wherein said film of insulating material has a thickness in a range of 0.0008 inch to 0.001 inch.

38. The instrument of claim 26 wherein said film of electrically conductive material has a thickness of 5 microns or less.

39. The instrument of claim 26 wherein said film of electrically conductive material is disposed less than completely around a circumference of said surface of said needle in said distal region thereof.

40. The instrument of claim 39 wherein said film of electrically conductive material is disposed over between ⅓ and ½ of said circumference of said needle.

41. The instrument of claim 26 wherein said film of electrically conductive material is disposed completely around a circumference of said surface of said needle in said distal region thereof.

42. The instrument of claim 26 or 18 wherein said needle is substantially 20 gauge in size.

43. The instrument of claim 42 further comprising a member slidably disposed in said passage with respect to said opening.

44. The instrument of claim 43 further comprising an actuator on said housing coupled to said member to enable a user to slidably advance and retract said member within said tube.

45. The instrument of claim 44 wherein said actuator is coupled to said member to enable said member to be extended distally through said opening.

46. The instrument of claim 45 wherein said member comprises a hollow second tube.

47. The instrument of claim 45 wherein said member comprises an optical fiber.

* * * * *